US005619136A

United States Patent [19]
Drury

[11] Patent Number: 5,619,136
[45] Date of Patent: Apr. 8, 1997

[54] DETECTION OF DISCONTINUITIES BELOW THE SURFACE OF MAGNETIZABLE MATERIAL USING DIFFERENTIALLY COUPLED SENSORS TO DETECT MAGNETIC FLUX LEAKAGE

[75] Inventor: John C. Drury, Swansea, United Kingdom

[73] Assignee: Silverwing, Limited, United Kingdom

[21] Appl. No.: 428,659

[22] Filed: Apr. 25, 1995

Related U.S. Application Data

[63] Continuation-in-part of Ser. No. 30,442, Mar. 24, 1993, abandoned.

[30] Foreign Application Priority Data

Feb. 11, 1992 [GB] United Kingdom ............... 9202846

[51] Int. Cl.$^6$ ..................... G01N 27/82; G01R 33/54
[52] U.S. Cl. ................. 324/242; 324/262; 324/235; 324/238
[58] Field of Search .................... 324/235, 242, 324/237, 228, 225, 238–241, 243, 260, 262, 217

[56] References Cited

U.S. PATENT DOCUMENTS

| | | | |
|---|---|---|---|
| 2,574,311 | 11/1951 | Zuschlag | 324/242 |
| 2,746,012 | 5/1956 | Price | 324/242 |
| 3,241,058 | 3/1966 | Quittner | 324/242 |
| 3,944,911 | 3/1976 | Tornblom | 324/242 |
| 4,218,651 | 8/1980 | Ivy | 324/227 |
| 4,243,939 | 1/1981 | Grossman et al. | 324/201 |
| 4,538,108 | 8/1985 | Huschelrath | 324/232 |
| 4,594,549 | 6/1986 | Smith et al. | 324/232 |
| 4,799,010 | 1/1989 | Muller | 324/240 |
| 4,808,924 | 2/1989 | Cecco et al. | 324/220 |
| 4,814,705 | 3/1989 | Saunderson | 324/225 |
| 4,823,082 | 4/1989 | Nasu et al. | 324/232 |
| 5,210,492 | 5/1993 | Hosohara et al. | 324/220 |
| 5,296,807 | 3/1994 | Kousek et al. | 324/235 |

FOREIGN PATENT DOCUMENTS

| | | |
|---|---|---|
| 0073017 | 2/1983 | European Pat. Off. . |
| 0238209 | 9/1987 | European Pat. Off. . |
| 2411211 | 3/1975 | Germany . |

*Primary Examiner*—Sandra L. O'Shea
*Assistant Examiner*—Jay M. Patidar
*Attorney, Agent, or Firm*—David P. Gordon

[57] ABSTRACT

An array of sensors is provided at or near the surface of a material arranged to detect magnetic flux leakage occurring when a magnetic field is induced in the material. The sensors in the array are coupled in respective pairs (differential pairs) such that when one partner of a respective pair overlies a discontinuity, a differential output signal is produced dependent on the difference between the output signals from the sensors of the respective differential pair. Because of the nature of the change of the flux leakage field produced by a discontinuity, respective partners of each pair of sensors are spaced relative to each other according to the invention. In one embodiment, partners of each sensor pair are spaced relative to one another both in the direction of travel of the apparatus and also in a direction transverse thereto. In another embodiment, each partner of a respective pair of sensors is spatially separated from the other partner of the respective pair by at least one partner of another pair of sensors. A warning is produced in response to the differential output signal to indicate that a discontinuity has been located. Typically the warning is only produced when the differential output signals are greater than a predetermined threshold value.

21 Claims, 4 Drawing Sheets

DETECTION OF DISCONTINUITIES BELOW THE SURFACE OF MAGNETIZABLE MATERIAL USING DIFFERENTIALLY COUPLED SENSORS TO DETECT MAGNETIC FLUX LEAKAGE

RELATED APPLICATIONS

This application is a continuation-in-part of application Ser. No. 08/030,442, filed Mar. 24, 1993, now abandoned.

BACKGROUND OF THE INVENTION

This invention relates to detecting magnetic discontinuities below the surface of magnetisable material using magnetic flux leakage techniques.

It is known from U.K. Patent Specification 2188156 that discontinuities such as cracks or pits below the surface of a specimen of magnetisable material can be detected by magnetising the material and sensing variations in leakage field near the surface of the specimen. The apparatus disclosed in U.K. Patent Specification 2188156 utilises an array of flux leakage sensors which are moved over the material surface in close proximity thereto. At successive locations in the direction of movement of the array, signals produced by each of the sensors in the array are recorded and subsequently the recorded values compared using appropriate signal processing apparatus, with an "average" of values recorded for each respective sensor at sensor locations successively before and successively after that particular location. The difference between the recorded value and the "average" gives an indication of magnetic discontinuity at a particular sensor location. Disadvantages with the apparatus and method disclosed in U.K. Patent 2188156 are two fold. Firstly, powerful signal processing apparatus is required to analyse the sensor output signals and produce a "grid reference" model corresponding to the area tested so that locations where a discontinuity has been detected by the sensors can be accurately related to their actual position over the actual area tested. Secondly, arising from the need to compare sensor signals at specific locations with signals from the same sensor at successive locations, and the results subsequently processed, the apparatus cannot be used to give a "real time" indication of discontinuities in the surface under test.

SUMMARY OF THE INVENTION

We have now devised apparatus for detecting discontinuities in magnetisable material, which overcomes the abovementioned disadvantages.

According to a first aspect of the present invention, there is provided apparatus for detecting discontinuities below the surface of magnetisable material, which apparatus comprises:

(a) a carriage movable in a predetermined direction of travel over the surface of said material;

(b) inducing means being movable with said carriage and for inducing a magnetic field in said material;

(c) an elongate array of sensors being movable with said carriage and extending transversely to the direction of travel of the carriage, each sensor being arranged to detect flux leakage at or near the surface of said material and produce an output signal indicative thereof, said sensors being coupled in respective pairs each comprising a first partner and a second partner, each respective pair being arranged to produce a differential output signal dependent on the difference between said output signals produced by first and second partners comprising each pair, the first and second partners of the respective pairs of sensors being spaced relative to one another both in the direction of travel of the carriage and also transversely thereto; and (d) warning themes arranged to be actuated in response to differential output signals produced by a said pair of sensors.

Since the sensors comprising each pair are electrically couple, where both sensors detect the same magnetic flux (i.e. where they are both positioned over homogeneous material) the signals will cancel one another out and no differential signal will be produced by the pair.

Where however one of the sensors is positioned over a discontinuity (e.g. a corrosion pit), the change in magnetic flux detected by that sensor will cause a change in the output from that sensor such that a differential output signal will be produced by the pair of sensors of which that sensor is a member.

It is clear that any variation or difference in signals produced by sensors comprising a respective pair will produce a (differential) output signal from the pair, and thereby actuate the warning means. It is preferred that the warning means is arranged to be actuated however when the differential output signal from a respective pair of sensors reaches or exceeds a predetermined (threshold) value. Advantageously, this predetermined (threshold) value is variable. In this instance any differential output signal produced by respective pairs will only actuate the warning means when the output signal is greater than a predetermined threshold level. This enables the method to be "fine tuned" to detect discontinuities representing cracks or pits greater than a pre-determined physical size, and to ignore noise less than a pre-determined level.

Typically, each respective pair is connected to warning means, preferably an audible or visible warning indicator arranged to detect an output signed from a respective pair of sensors. Advantageously each respective pair is connected to a respective warning indicator.

The array is typically mounted on a carriage which is moved over the surface of the material; once a warning indicator has been actuated, the carriage is stopped automatically and the two possible positions (i.e. corresponding to the respective positions of the members of the activated sensor pair) of the discontinuity may be physically marked on the surface of the material immediately above those two possible sites (typically by means of paint mark or the like), either manually or automatically. Subsequently, after the desired area of the surface of the material has been tested, the marked positions are re-tested by calibrated apparatus such as ultrasound non-destructive testing equipment, so as to give a quantitative value of the depth (and/or size) of the discontinuity (representing the crack or pit) below the surface of the material.

According to a second aspect or the invention, there is provided apparatus for detecting discontinuities below the surface of magnetisable material, which apparatus comprises:

(a) inducing means for inducing a magnetic field in said material;

(b) an array of sensors, each of said sensors being arranged to detect and produce an output signal indicative of flux leakage at or near the surface of said material, said sensors being electrically coupled in respective pairs, each pair of said sensors being arranged to produce a differential output signal dependent on the difference between said output signals produced by the individual sensors comprising each pair, each member of a respective pair of said sensors being spaced from the other member of said respective pair by a member of at least one other respective pair of sensors; and (c) warning means arranged to be actuable in response to a differential output signal produced by a said pair of sensors.

It is preferred that the inducing means, and the array of sensors, (and also preferably the warning means) are mounted on a movable carriage or trolley, which can be moved relative to a ground surface on wheels or the like. It is preferred that sensors comprising a pair of sensors are separated from one another by a plurality of intermediate sensors, said intermediate sensors comprising members of other pairs of sensors. It is preferred that the sensors used are solid state, preferably of the hall effect type; alternatively magnetodiodes or induction coil sensors may be used.

Advantageously, calibration means is provided to inhibit actuation of the warning means where differential signals produced by respective pairs of sensors are below a predetermined threshold level. The calibration means is preferably adjustable such that the threshold level may be selectively varied.

Typically, the warning means will be in the form of an audible or visible indicator. Advantageously respective warning means are provided for each respective pair of sensors. In a preferred embodiment, the warning means comprise an array of warning lights, preferably arranged such that a pair of lights corresponds to a respective pair of sensors.

Typically, the magnet will be a permanent magnet, advantageously of "horseshoe" type, although an electromagnet may be used as an alternative.

It is preferred that the array of sensors is provided on a carrier member which carrier member is pivotally mounted on the carriage or trolley, Advantageously, the carrier or trolley is provided with independent drive means, such as a motor or the like arranged to power the apparatus.

The invention will now be further described in a specific embodiment by way example only, with reference to the accompanying drawings.

DETAILED DESCRIPTION OF THE PREFERRED EMBODIMENTS

Figure 3:
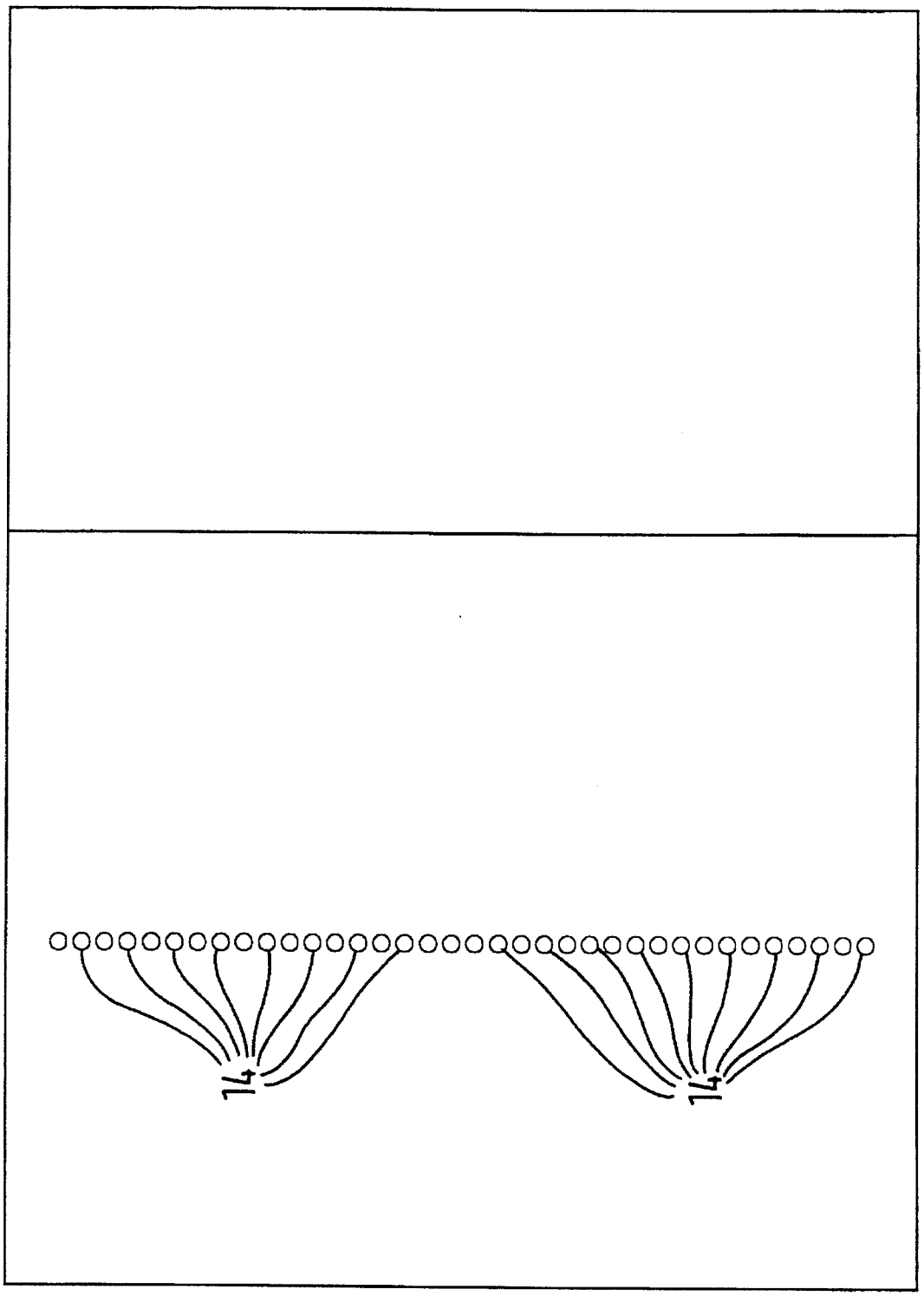
FIG. 3 is a plan view of the apparatus shown in FIGS. 1 and 2.

Referring to the drawings, apparatus for detecting magnetic discontinuities in magnetisable material (such as corrosion pits or cracks in steel plate 16) is shown. The apparatus, generally designated 1, comprises a carriage or trolley 2 having wheels 4. A carrier 9 is pivotally mounted to the trolley 2 by means of pivot mountings 5. The trolley 2 comprises two compartments, a forward compartment housing balancing and trigger circuits and visual alarm in the form of an array of L.E.D's (best shown in FIG. 3) 14. The rear compartment contains DC batteries 12, a drive motor and gearbox 3, and the trolley drive wheels 4. The carrier 9 rides on a series of wheels 15 and seats a horseshoe magnet assembly comprising a magnet bridge 11 and neodymium-iron-boron rectangular magnets 13. A sensor head 6, also mounted on carrier 9, houses a linear array of thirty six Hall effect 7. It is attached to the magnet carriage by the pivot arms 8 and connected to the balance and trigger circuitry by cables 10.

The magnets 13 are seated in the carrier 9 so as to be close to the surface of a steel plate 16 under examination, the gap between the pole pieces and the surface of the steel plate typically being adjustable. The sensor head comprises a rectangular box the lower half of which is made of a material known commercially as nylatron, chosen for its resistance to wear and abrasion. A printed circuit board (not shown) to which the sensor array is attached is fitted into the lower box and a lid of material commercially available under the trade mark Tufnol fitted to seal the sensors from dirt and moisture. The pivot arms 8 are adjusted to allow a small gap between the sensor head 6 and the steel plate 16 under examination. They allow the sensor head to ride upwards if the chamfered edges of the sensor head 7 encounter protrusions or undulations in the steel plate surface.

Figure 4:
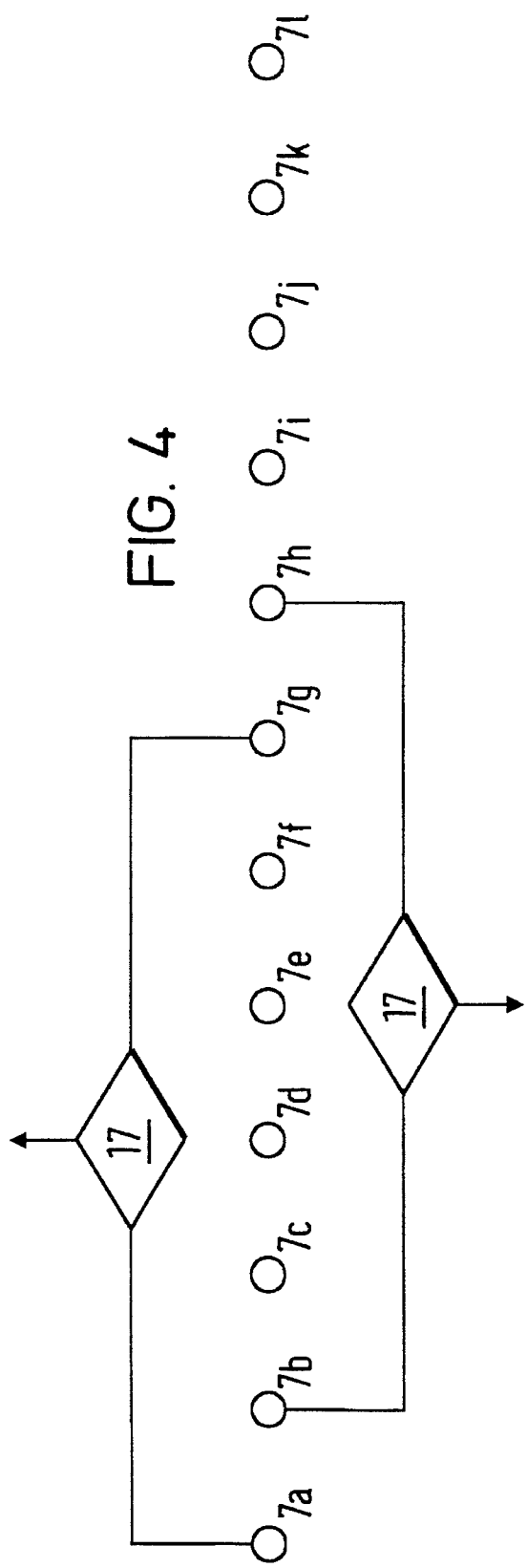
FIG. 4 is a schematic exemplary view of a first embodiment of sensor arrangement for use in the apparatus shown in FIGS. 1 to 3.

The sensors in the array am electrically connected in respective pairs (referred to as differential pairs) to balance and trigger circuitry 17 by connection cables 10. As is best shown in FIG. 4 (where a part of the sensor array only is shown), the pairs of differential sensors 7, are arranged in "overlapping" relationship with five sensors from adjacent differential pairs being located intermediate the sensor partners comprising a first differential pair. In the part of the sensor array shown in FIG. 4, the sensors are therefore connected in the following partner pairs: 7a & 7g; 7b & 7h; 7c & 7i; 7d & 7j; 7e & 7k; 7f & 7l. The spacing between the centres of adjacent sensors in the array is typically of the order of 7.5 mm, whereas the spacing between sensors comprising a differential pair is typically of the order of 45 mm. It has been observed that the magnetic field extension at the site of a discontinuity in a direction transverse to the direction of movement of the carriage may be 4 to 5 times greater that the dimension of the discontinuity in that direction, the spacing chosen for a differential pair of sensors should ensure that the signals from a typical defect do not tend to be self cancelling.

Figure 1:
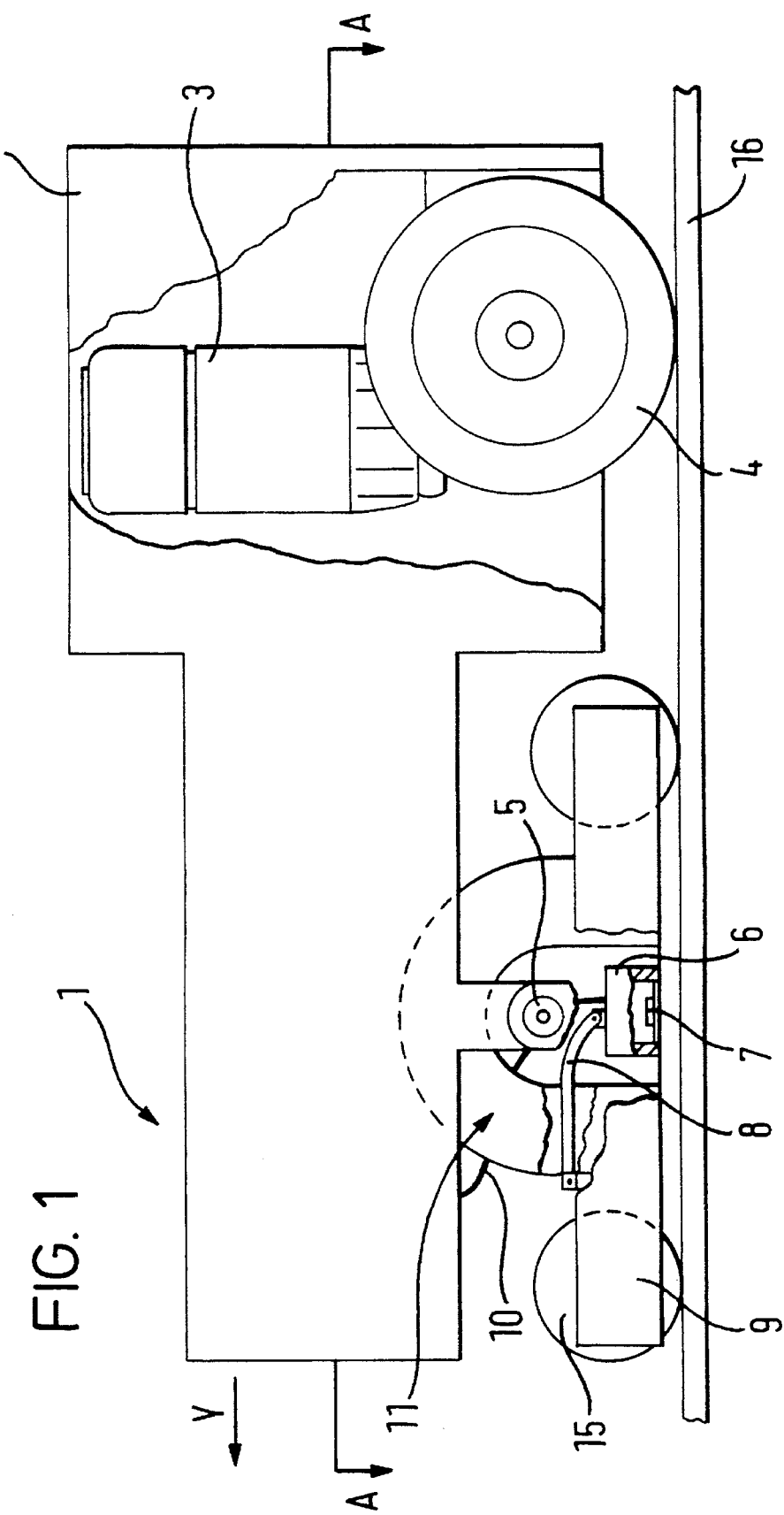
FIG. 1 is a partly diagrammatic side view of apparatus for detecting magnetic discontinuities.
Figure 2:
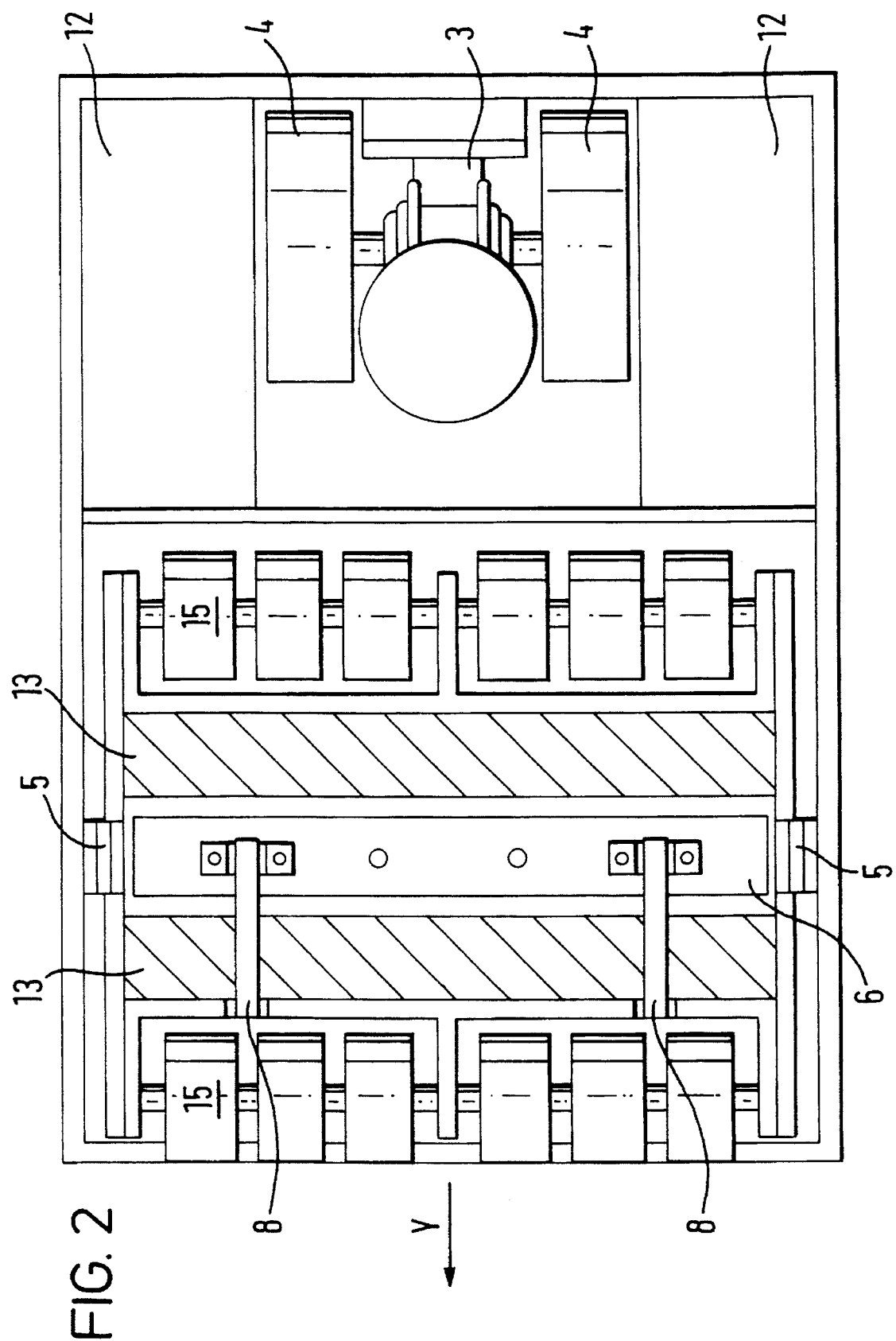
FIG. 2 is a sectional plan view on the line A—A of the apparatus shown in FIG. 1.

With the apparatus in position as shown in FIG. 1, the magnets 11 induce a magnetic field in the steel plate 16 under examination. Flux leakage from the plate 16 will vary depending on the presence or absence of magnetic discontinuities (such as pits or cracks) in the thickness of the plate. Each of the Hall effect sensors 7 in the array produces an electrical output signal proportional to the flux leakage at a corresponding point above the plate 16. Since the sensors 7 are arranged in differential pairs as described above, where both sensors comprising a pair lie above homogenous portions of the plate (i.e. where there are no cracks or pits) the respective output signals from each of the sensors comprising that pair will be substantially equal. In this case the differential signal produced by the balancing circuitry for that pair will be zero. Where however one of the sensor partners 7 comprising a pair lies over a magnetic discontinuity whilst the other sensor partner 7 does not, each sensor partner comprising the pair will produce a different output signal in response to different values of flux leakage detected. This difference in individual sensor output signal results in a differential output signal for that respective pair of greater than zero being output from the balancing and triggering circuitry.

It has been found that significantly enhanced results are achieved where the vertical component of the induced flux leakage field is sensed. This provides improved defect detection for discontinuities relatively deep below the surface and reduces distortion and noise effects caused by surface roughness, lift off of the carriage from the surface and so on.

Differential signals which exceed a predetermined calibration threshold (to reduce the effects of noise) trigger an output voltage to two of thirty six bi-color light emitting diodes 14 corresponding to the differential pair of sensors detecting the discontinuity, changing the colour from green (balanced) to red (discontinuity). A ten turn digital potentiometer is provided to adjust the threshold value dieting calibration.

In use, the apparatus is moved at a steady speed across the surface of the specimen plate by the motor or manually. In the absence of any discontinuity there will be no output from the differential pairs of sensors to the trigger circuits, and all LED's will show in the green state. As a sensor passes over a discontinuity the balance with its pair is disturbed and an output signal fed to the trigger circuit; if this exceeds the threshold level, the corresponding LED's are changed to red. The operator stops the apparatus and marks the possible location of the discontinuity on the surface of the specimen plate.

In some circumstances, this apparatus has been shown to be capable of detecting corrosion pits penetrating to a depth of less than 30% of wall thickness in 6 to 10 mm plate.

Figure 5:
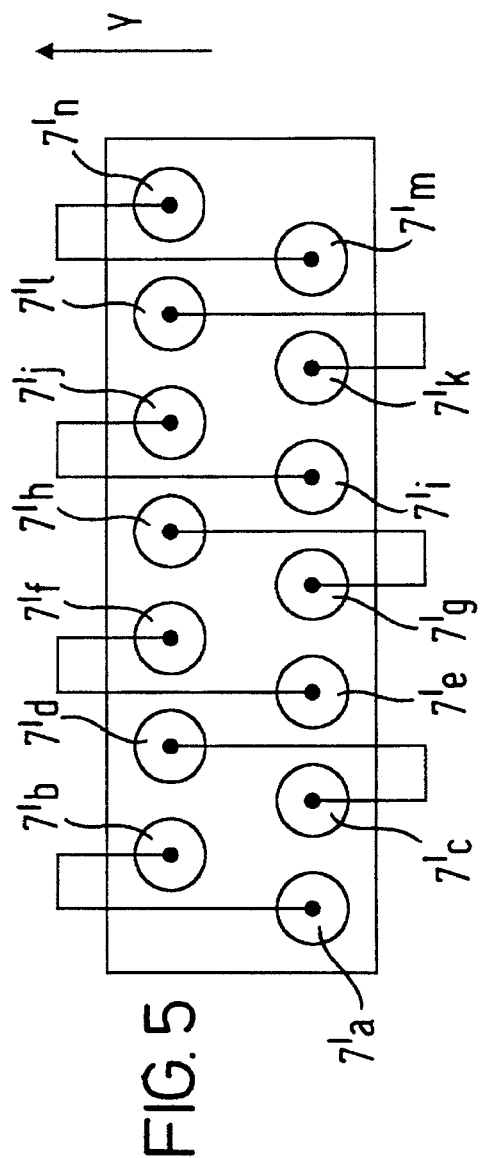
FIG. 5 is a schematic exemplary view of a second embodiment of sensor arrangement for use in the apparatus of FIGS. 1 to 3.

Referring now to FIG. 5, there is shown an alternative (and preferred) arrangement of sensors 7 which has been found to provide advantages over the sensor arrangement shown in FIG. 4.

In the sensor array shown in FIG. 5, sensors 7 are coupled in differential pairs which each have first and second partners spaced in mutually perpendicular directions (in the direction of travel, Y, of the apparatus and transversely thereto). For example, the first sensor pair in the arrangement (the pair closest to the leftmost edge of the drawing) comprises a first partner 7'a coupled to a diagonally spaced second partner 7'b. The second sensor pair comprises partners 7'c and 7'd and so on (7'e, 7'f, 7'g, 7'h, 7'i, 7'j, 7'k, 7'l) along the array ending tip with the final sensor pair comprising coupled sensor partners 7'm and 7'n. The distance between a first partner of a first pair and a first partner of a second pair is substantially the same as the distance between the first partner of the first pair and the second partner of the first pair as shown in FIG. 5.

A disadvantage with the sensor array arrangement shown in FIG. 4 is that, due to the large separation of the sensor partners of each sensor pair it cannot be easily identified which of the two sensor partners is situated over the discontinuity. Thus both possible sites must be investigated. The reason for the large separation is (as mentioned above) because of the fact that the flux leakage field perpendicular to the direction of carriage travel extends between three and five times the dimension of the discontinuity. There is thus the danger that sensor partners which are not largely separated from each other would both record a discontinuity and their respective signals signals would thus be cancelled.

The sensor array arrangement shown in FIG. 5 makes use of the discovery that the flux leakage field in the direction of travel (direction Y) is substantially less extensive (typically less than half) than its extension perpendicular to the direction of travel.

Sensor partners 7'a and 7'b, comprising an exemplary differentially coupled pair, may therefore be relatively closely spaced providing there is a sufficient spacing in the direction of travel. It should be noted that it is also important that the sensors remain spaced transversely to the direction of travel. This is because subsurface discontinuities (such as subsurface cracks) are frequently linear and there is a danger that a sensor pair would have both partners simultaneously overlying a linear crack running in the direction of travel of the apparatus which would consequently not be noticed.

In the arrangement shown in FIG. 5, each differentially coupled pair of sensors is connected to balance and trigger circuitry to produce a differential electrical output and warning in the same or similar manner to that described above. In this case, because partner sensors comprising each pair are relatively closely spaced (typically approximately 15 mm) although two LED's 14 are still illuminated, these are now adjacent LED's corresponding to adjacent sensor partners 7' and an ultrasonic transducer can be used to localise and pin point the discontinuities exact position.

A further advantage is that, because the sensor partners 7' are relatively closely spaced, Eddy current signals generated by movement of the carriage 2 are likely to be close in amplitude and phase at the sensors partners 7' comprising each sensor pair. Such Eddy current signals are thereby cancelled out reducing signal noise.

What is claimed is:

1. Apparatus for detecting discontinuities below a surface of a magnetisable material, which apparatus comprises:

(a) a carriage movable in a predetermined direction of travel over the surface of the material;

(b) inducing means being movable with said carriage and for inducing a magnetic field in the material;

(c) an elongate array of sensors being movable with said carriage and extending transversely to the direction of travel of said carriage, each sensor being arranged to detect a flux leakage at or near the surface of the material and produce an output signal indicative thereof, said sensors being coupled in respective pairs each comprising a first partner and a second partner, each respective pair being arranged to produce a differential output signal dependent on a difference between said output signals produced by first and second partners comprising each pair, said first and second partners of said respective pairs of sensors being spaced relative to one another both in the direction of travel of said carriage and in a direction transverse to the direction of travel of said carriage; and (d) warning means arranged to be actuated in response to said differential output signals produced by said pairs of sensors.

2. Apparatus according to claim 1, wherein said elongated array of sensors is arranged such that a first rank of sensors is provided extending substantially perpendicularly to the direction of travel of the carriage, a second rank of sensors being provided spaced from said first rank and substantially parallel thereto, said first rank comprising a plurality of first partners of respective pairs whereas said second rank comprises a plurality of second partners of respective pairs.

3. Apparatus according to claim 1, wherein said inducing means is arranged to induce a magnetic field in said material which has a vertical component perpendicular to the plane of the surface of the material, said sensors being arranged to produce respective output signals indicative of flux leakage of said vertical component of said magnetic field.

4. Apparatus according to claim 1, wherein the distance between a first partner of a first respective pair and a first partner of a second respective pair is substantially the same as the distance between said first partner of said first respective pair and the second partner of said first respective pair.

5. Apparatus according to claim 1, wherein said sensors comprise solid state devices.

6. Apparatus according to claim 5, wherein said sensors comprise hall effect sensors.

7. Apparatus according to claim 1, wherein calibration means is provided to inhibit actuation of the warning means where differential signals produced by respective pairs of said sensors are below a predetermined threshold level.

8. Apparatus according to claim 7, wherein said calibration means is adjustable such that said threshold level is selectively varied.

9. Apparatus according to claim 1, wherein said warning means is actuable to produce an audible or visible warning indication.

10. Apparatus according to claim 1, wherein the warning means is arranged, when actuated, to give an indication of identity of the respective pair of sensors the differential output from which has caused the warning means to be actuated.

11. Apparatus according to claim 10, wherein separate respective warning means are provided for each respective pair of sensors.

12. Apparatus for detecting discontinuities below a surface of a magnetisable material, which apparatus comprises:

(a) inducing means for inducing a magnetic field in the material;

(b) an array of sensors, each of said sensors being arranged to detect flux leakage at or near the surface of the material and produce an output signal indicative thereof, said sensors being electrically coupled in respective pairs each comprising a first partner and a second partner, each pair of said sensors being arranged to produce a differential output signal dependent on a difference between said output signals produced by said first partner and said second partner, each partner of a respective pair of sensors being spaced from the other partner of said respective pair by a partner of at least one other respective pair of sensors; and (c) warning means arranged to be actuated in response to said differential output signal produced by said pair of sensors.

13. Apparatus according to claim 12, wherein at least the inducing means and the array of sensors are mounted on a movable carriage or trolley.

14. Apparatus according to claim 12, wherein the sensors are arranged in a substantially linear array.

15. Apparatus according to claim 12, wherein said sensors comprise solid state devices.

16. Apparatus according to claim 15, wherein said sensors comprise Hall effect sensors.

17. Apparatus according to claim 12, wherein calibration means is provided to inhibit actuation of the warning means where differential signals produced by respective pairs of said sensors are below a predetermined threshold level.

18. Apparatus according to claim 17, wherein said calibration means is adjustable such that said threshold level is selectively varied.

19. Apparatus according to claim 12, wherein said warning means is actuable to produce an audible or visible warning indication.

20. Apparatus according to claim 12, wherein the warning means is arranged, when actuated, to give an indication of identity of the respective pair of sensors the differential output from which has caused the warning means to be actuated.

21. Apparatus according to claim 20, wherein separate respective warning means are provided for each respective pair of sensors.

* * * * *